United States Patent [19]

Suzuki et al.

[11] 4,025,526

[45] May 24, 1977

[54] PROCESS FOR PRODUCING THIAZOLES

[75] Inventors: Fumio Suzuki; Mitsuo Tanaka; Yoshiaki Mera, all of Funabashi, Japan

[73] Assignee: Nissan Chemical Industries, Ltd., Tokyo, Japan

[22] Filed: Oct. 2, 1975

[21] Appl. No.: 618,844

[30] Foreign Application Priority Data

Oct. 3, 1974 Japan ............................ 49-114239
Oct. 16, 1974 Japan ............................ 49-118884

[52] U.S. Cl. .......................................... 260/302 R
[51] Int. Cl.² ...................................... C07D 277/22
[58] Field of Search ................................ 260/302 R

[56] References Cited

UNITED STATES PATENTS 3,501,488   3/1970   Colebourne .................. 260/302 R Primary Examiner—R.J. Gallagher
Attorney, Agent, or Firm—Oblon, Fisher, Spivak, McClelland & Maier

[57] ABSTRACT

An improvement in a process for producing 2-methylthiazole or 2,4-dimethylthiazole by reacting diethylamine, ethylidene-ethylamine or diisopropylamine with sulfur, the improvement comprising conducting said reaction in a reactor wherein a carbon layer has been formed on the inner surface of the walls of said reactor.

8 Claims, No Drawings

PROCESS FOR PRODUCING THIAZOLES

BACKGROUND OF THE INVENTION

1. Field Of The Invention

The present invention relates to a process for producing 2-methylthiazole or 2,4-dimethylthiazole.

2. Description Of The Prior Art

The above-mentioned thiazoles are useful as intermediates for preparation of agricultural chemicals and pharmaceutical compounds. 2-methylthiazole is especially useful as an intermediate for preparation of many active ingredients of agricultural insecticides. Processes for producing 2-methylthiazole and 2,4-dimethylthiazole are known and have been disclosed in Japanese Pat. No. 26861/1968. The chemical reactions involved in these processes are as follows:

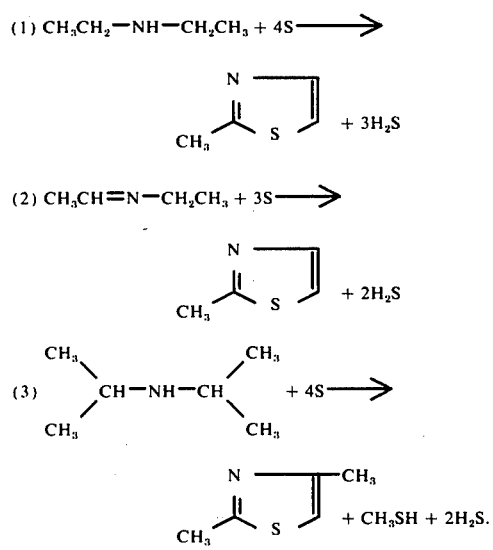

In these known processes, a dialkylamine or dialkylimine is fed with nitrogen into a reactor where it mixes with a separate flow of sulfur fed with nitrogen. Upon mixing at 250°–750° C, reaction ensues. In accordance with this conventional process, the yield of the object product is quite low, about 40% or less. In order to utilize these reactions on an industrial scale, it has been desired to improve the yield. Using conventional considerations, the present inventors have tried various catalysts or additives in the above-mentioned reactions. However, advantageous effects have not been found. Consequently, there remains a need for an improvement in the conventional process which is capable of increasing the resultant product yield.

SUMMARY OF THE INVENTION

Accordingly, it is an object of this invention to provide a process for producing 2-methylthiazole or 2,4-dimethylthiazole in higher yields.

Briefly, this and other objects of this invention, as will hereinafter become clear from the ensuing discussion, have been attained by providing a process for producing 2-methylthiazole or 2,4-dimethylthiazole comprising reacting diethylamine, ethylidene-ethylamine or diisopropylamine with sulfur in a reactor whose inner surface is coated with a carbon layer.

DETAILED DESCRIPTION OF THE PREFERRED EMBODIMENTS

As can be seen below, when diethylamine, for example, is used as the starting material, the yield of 2-methylthiazole can be increased to a level higher than 60% so as to make the reaction very suitable for industrial operation. This is a typical result of the improvement of the present invention.

In accordance with the process of this invention, a carbon layer is formed on the inner surface of the reactor before the starting materials are fed therein. For example, the carbon layer may be formed on the inner surface of the reactor by feeding a hydrocarbon and oxygen or sulfur therein and reacting them. Thereafter, diethylamine, ethylidene-ethylamine or diisopropylamine and sulfur can be fed into the reactor which is covered with the carbon layer and reacted to produce 2-methylthiazole or 2,4-dimethylthiazole.

In the process of this invention, the reactor can be made of glass or metal and preferably is made of Pyrex glass or stainless steel. Suitable methods of forming the carbon layer on the inner surface of the reactor include the following. A hydrocarbon, e.g., n-hexane, toluene, and the like and sulfur or oxygen can be mixed in the reactor at 400°–500° C, whereby they will react and form a carbon layer by dehydrogenation. Alternatively, a trialkylboron can be decomposed by heating it in the reactor, thereby forming a carbon layer on the inner surface of the reactor. In industrial operation, it is advantageous to react the hydrocarbon with sulfur to form the carbon layer on the inner surface of the reactor and thereafter change the feed of the hydrocarbon to the appropriate amine feed, whereby the amine will react with sulfur to produce the object products.

The method used to form the carbon surface in the reactor is not critical and other conventional techniques may be used.

In order to separate the object product from the reaction mixture, well-known conventional methods such as distillation may be used.

The yields of 2-methylthiazole in the process of this invention were determined by varying the reaction temperature, the reaction time (retention time), the equivalent ratio of sulfur to the amine and the type of carrier gas used in the reaction of the amine with sulfur. The results are shown in Tables 1–4. The tests were conducted in accordance with the process and apparatus of Example 4 for the experiments of Tables 1, 2 and 3, and in accordance with the process and the apparatus of Example 1 for the experiments of Table 4.

Table 1

| Effect of reaction temperature on the yield of 2-methylthiazole | |
|---|---|
| Reaction temperature (° C) | Yield of 2-methylthiazole (%) |
| 400 | 63.9 |
| 430 | 66.2 |
| 450 | 67.0 |
| 500 | 58.7 |
| 550 | 56.9 |

Notes:
Reaction time (retention time) : 4 seconds;
Equivalent ratio of sulfur to diethylamine : 1.2 : 1.

Table 2

| Effect of reaction time on the yield of 2-methylthiazole | |
|---|---|
| Reaction time (retention time) (seconds) | Yield of 2-methylthiazole (%) |
| 2 | 60.6 |

Table 2-continued

Effect of reaction time on the yield of 2-methylthiazole

| Reaction time (retention time) (seconds) | Yield of 2-methylthiazole (%) |
|---|---|
| 3 | 65.0 |
| 4 | 67.0 |
| 6 | 48.6 |
| 8 | 44.7 |

Notes:
Reaction temperature: 450° C;
Equivalent ratio of sulfur to diethylamine: 1.2 : 1.

Table 3

Effect of the equivalent ratio of sulfur to diethylamine on the yield of 2-methylthiazole

| Equivalent ratio of sulfur to diethylamine | Yield of 2-methylthiazole (%) |
|---|---|
| 0.8 : 1 | 51.3 |
| 1 : 1 | 58.5 |
| 1.1 : 1 | 63.1 |
| 1.2 : 1 | 67.0 |
| 1.4 : 1 | 59.8 |

Notes:
Reaction temperature: 450° C;
Reaction time: 4 seconds.

Table 4

Effect of type of carrier gas on the yield of 2-methylthiazole

| Diethylamine mixed gas fluid | | Sulfur mixed gas fluid | | Yield of 2-methyl-thiazole (%) |
|---|---|---|---|---|
| Type of carrier gas | Flow rate of carrier gas | Type of carrier gas | Flow rate of carrier gas (l/hr) | |
| nitrogen | 40 l/hr. | nitrogen | 40 | 60.6 |
| " | " | H$_2$S | 40 | 62.0 |
| benzene | 330 g/hr. | nitrogen | 40 | 61.0 |
| toluene | 330 g/hr. | " | 40 | 61.5 |
| none | — | " | 40 | 54.7 |

Notes:
Reaction temperature: 500° C; Reaction time: 4 seconds;
Equivalent ratio of sulfur to diethylamine: 1.1 : 1.

These results indicate the preferred reaction conditions as follows. From the data of Table 1, the reaction temperature is preferred to be in the range of 400°–550° C, especially 400°–450° C, in order to attain the highest yield. When it is lower than 400° C, the amount of the unreacted material is relatively high and when it is higher than 550° C, the amounts of by-products of thiazoles, acetonitrile, and carbon disulfide are high. From the data of Table 2, the reaction time (retention time in the reactor) is preferred to be in the range of 2 – 8 seconds, especially 2 – 4 seconds. From the data of Table 3, the equivalent ratio of sulfur to diethylamine is preferred to be in the range of 0.8 : 1–1.4 : 1, especially 1.1 : 1 – 1.2 : 1. From the data of Table 4, it is preferable to conduct the reaction in an atmosphere of an inert gas, and nitrogen, benzene, toluene and hydrogen sulfide are suitable carrier gases. The reactions of diethylamine with sulfur have been illustrated in detail in the above data. However, the same results and conclusions can be applied to the reactions of ethylidene-ethylamine or diisopropylamine with sulfur.

Having generally described the invention, a more complete understanding can be obtained by reference to certain specific examples, which are provided for purposes of illustration only and are not intended to be limiting unless otherwise specified.

EXAMPLE 1

In a vaporizer maintained at 400° C, n-hexane was fed at a rate of 700 g/hr., and nitrogen gas was fed at a rate of 40 liter/hr. to form a mixed gas. In another vaporizer maintained at 580° C, sulfur was fed at a rate of 520 g/hr. (a molar ratio of 20 relative to n-hexane), and nitrogen gas was fed at a rate of 40 liter/hr. to form a mixed gas. Both of the mixed gases were fed into a reactor made of Pyrex glass (having an inner diameter of 75 mm and a length of 1000 mm) to mix them. The mixture was passed through the reactor at 450°–500° C using 10 seconds retention time for a total of about 30 minutes, whereby a carbon layer was formed on the inner surface of the reactor. Then, 2-methylthiazole was produced by the reaction of diethylamine with sulfur. In the vaporizer maintained at 400° C, diethylamine was fed at a rate of 750 g/hr., and nitrogen gas was fed at a rate of 40 liter/hr. to form a mixed gas.

In another vaporizer maintained at 580° C, sulfur was fed at a rate of 1,600 g/hr. (an equivalent ratio of 1.2 relative to diethylamine) and nitrogen gas was fed at a rate of 40 liter/hr. to form a mixed gas. Both of the mixed gases were fed into the reactor (having a carbon layer already formed on its inner surface) to react them at 450° – 500° C using a retention time of 4 seconds for a total of 1 hour. A part of the reaction mixture was sampled and was analyzed by gas chromatography. The results are shown in Table 5. The conditions used in the gas chromatographic analysis are as follows:

| | |
|---|---|
| Type of gas chromatograph: | GC-3AH (manufactured by Shimazu Seisakusho,K.K.) |
| Length of column | 1 m |
| Temperature of column: | 180° C |
| Filler of column: | Porapak-Q (manufactured by Nishio Kogyo K.K.) |
| Carrier gas: | helium |
| Pressure of carrier gas: | 1 kg/cm$^2$ G |

Table 5

| Products | Yield per 1 hour (g) | Yield (%) |
|---|---|---|
| 2-methylthiazole | 670 | 65.9 |
| thiazole | 39.3 | 4.5 |
| acetonitrile | 29.5 | 7.0 |
| carbon disulfite | 30.0 | — |

Note: The yield was measured by gas chromatography and the molar yield is based on the amount of diethylamine used.

$$\text{Yield (\%)} = \frac{\left(\frac{\text{Yield of product}}{\text{molecular weight of product}}\right)}{\left(\frac{\text{amount of amine fed}}{\text{molecular weight of amine fed}}\right)} \times 100$$

EXAMPLE 2

The process for forming the carbon layer on the inner surface of the reactor of Example 1 was repeated using the same reactor except for feeding air at a rate of 300 liter/hr. instead of sulfur. The reaction of diethylamine with sulfur and the gas chromatographic analysis were conducted under the same conditions as used in Example 1. The yield of 2-methylthiazole was 60.5%.

EXAMPLE 3

The process for forming the carbon layer on the inner surface of the reactor of Example 1 was repeated using the same reactor except for feeding a tetrahydrofuran solution of tri-n-decaneboron (30 wt.%) at a rate of 700 g/hr. into a vaporizer maintained at 350° C, and for feeding the gas into the reactor at 400° C for 2 hours to form a carbon layer. The reaction and the analysis of Example 1 were repeated in the reactor using the same conditions. The yield of 2-methylthiazole was 63.2%.

EXAMPLE 4

The process for forming a carbon layer on the inner surface of the reactor of Example 1 was repeated except for using a reactor made of stainless steel (SUS 27) (having an inner diameter of 75 mm and a length of 1000 mm) instead of the reactor made of Pyrex glass. The reaction and the analysis of Example 1 were repeated in the reactor using the same conditions. The yield of 2-methylthiazole was 63.2%.

EXAMPLE 5

The process for forming the carbon layer on the inner surface of the reactor of Example 1 was repeated except for using a reactor made of stainless steel (SUS 27) and using toluene instead of n-hexane (an equivalent ratio of 2 relative to sulfur). The reaction and the analysis of Example 1 were repeated in the reactor using the same conditions. The yield of 2-methylthiazole was 61.1%.

EXAMPLE 6

A carbon layer was formed on the inner surface of the reactor in accordance with the process of Example 4. Into a vaporizer maintained at 400° C, a benzene solution of 28 wt. % ethylidene-ethylamine was fed at a rate of 1080 g/hr. and nitrogen gas was fed at a rate of 40 liter/hr. to form a mixed gas. Into another vaporizer maintained at 580° C, sulfur was fed at a rate of 490 g/hr. and nitrogen gas was fed at a rate of 40 liter/hr. to form a mixed gas. Both of the mixed gases were fed into the reactor at 450° – 500° C under a retention time of 8 seconds and reacted for a total of 1 hour. In accordance with the method of Example 1, the reaction mixture was analyzed showing that 2-methylthiazole was obtained at a rate of 257.9 g/hr. The yield was 61.2%.

REFERENCE EXAMPLE 1

The process of Example 1 was repeated using the same conditions and the same analysis except for using a reactor made of Pyrex glass without formation of a carbon layer on its inner surface. The yield of 2-methylthiazole was 45.8%.

REFERENCE EXAMPLE 2

The process of Example 4 was repeated using the same conditions and the same analysis except for using a reactor made of stainless steel without formation of a carbon layer on its inner surface. The yield of 2-methylthiazole was 44.4%.

EXAMPLE 7

In a vaporizer maintained at 400° C, n-hexane was fed at a rate of 700 g/hr. and nitrogen gas was fed at a rate of 40 liter/hr. to form a mixed gas. On the other hand, in another vaporizer maintained at 580° C, sulfur was fed at a rate of 520 g/hr. (a molar ratio of 20 relative to n-hexane) and nitrogen gas was fed at a rate of 40 liter/hr. to form a mixed gas.

Both of the mixed gases were fed into a reactor made of stainless steel (SUS 27) (having an inner diameter of 75 mm and a length of 1000 mm) at 450° – 500° C using a retention time of 10 seconds for a total of about 30 minutes to form a carbon layer on the inner surface of the reactor. The feed of n-hexane was stopped and replaced by a feed of diisopropylamine to react the latter.

In a vaporizer maintained at 400° C, diisopropylamine was fed at a rate of 955 g/hr. and nitrogen gas was fed at a rate of 40 liter/hr. to form a mixed gas. Also, in a vaporizer maintained at 580° C, sulfur was fed at a rate of 1574 g/hr. (1.3 equivalents relative to diisopropylamine) and nitrogen was fed at a rate of 40 liter/hr. to form a mixed gas. Both of the mixed gases were fed into the reactor at 450° C using a retention time of 4 seconds for reaction for a total of about 1 hour. A part of the reaction mixture was sampled and analyzed by gas chromatography. The amount of 2,4-dimethylthiazole formed was 438 g giving a yield of 59.0% (based on diisopropylamine). The conditions used in the gas chromatographic analysis are as follows:

| | |
|---|---|
| Type of gas chromatograph: | GC-4AH (manufactured by Shimazu Seisakusho K.K.) |
| Length of column: | 3 m |
| Temperature of column: | 140° C |
| Filler of column: | polyethyleneglycol 20 wt.% on a carrier of zeolite 545. |
| Carrier gas: | helium |
| Pressure of carrier gas: | 1 kg/cm²G. |

EXAMPLES 8, 9 and 10

The process of Example 7 was repeated using the same apparatus except for varying the reaction temperature, the reaction time and the equivalent ratio of sulfur to isopropylamine. In accordance with the method of Example 7, an analysis for 2,4-dimethylthiazole was conducted. The results are shown in Table 6, together with the results of Example 7.

Table 6

| Ex. | Reaction Temperature (° C.) | Reaction time (sec) | Equivalent ratio of sulfur to diisopropylamine | Yield (%) |
|---|---|---|---|---|
| 7 | 450 | 4 | 1 : 1.3 | 59.0 |
| 8 | 450 | 6 | 1 : 1.2 | 53.6 |
| 9 | 500 | 4 | 1 : 1.2 | 56.8 |
| 10 | 550 | 4 | 1 : 1.2 | 53.0 |

REFERENCE EXAMPLE 3

The process of Example 7 was repeated using the same conditions and the same analysis except for using a reactor made of stainless steel without formation of a carbon layer on its inner surface. The yield of 2,4-dimethylthiazole was 41.0%.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A process for producing thiazoles which comprises forming a carbon layer on the walls of a reactor by reacting a hydrocarbon with sulfur or oxygen, or by thermally decomposing trialkylboron; and subsequently reacting diethylamine or ethylidene-ethylamine with sulfur to produce 2-methylthiazole or reacting diisopropylamine with sulfur to produce 2,4-dimethylthiazole.

2. The process of claim 1, wherein diethylamine, ethylidene-ethylamine or diisopropylamine is fed into the reactor with an inert carrier gas and sulfur is separately fed with an inert carrier gas.

3. The process of claim 1, wherein diethylamine, sulfur and an inert gas are fed into a reactor having a carbon layer on its inner surface.

4. The process of claim 1, wherein ethylidene-ethylamine, sulfur and an inert gas are fed into a reactor having a carbon layer on its inner surface.

5. The process of claim 1, wherein diisopropylamine, sulfur and an inert gas are fed into a reactor having a carbon layer on its inner surface.

6. The process of claim 1, wherein the product is 2-methylthiazole and the reactants are diethylamine or ethylidene-ethylamine and sulfur.

7. The process of claim 1, wherein the product is 2,4-dimethylthiazole and the reactants are diisopropylamine and sulfur.

8. The process of claim 1, wherein the reaction temperature is from 400° – 550° C, the retention time of the gases in the reactor is 2 – 8 sec., and the equivalent ratio of sulfur to the reactant amine is 0.8 : 1 – 1.4 : 1.

* * * * *